(12) United States Patent
Kwon et al.

(10) Patent No.: US 11,433,558 B2
(45) Date of Patent: Sep. 6, 2022

(54) FLEXIBLE DRIVE MANIPULATOR

(71) Applicants: KOREA ADVANCED INSTITUTE OF SCIENCE AND TECHNOLOGY, Daejeon (KR); EASYENDO SURGICAL, INC., Daejeon (KR)

(72) Inventors: Dong Soo Kwon, Daejeon (KR); Jae Min You, Daejeon (KR); Joon Hwan Kim, Daejeon (KR); Jeong Do Ahn, Daejeon (KR); Han Soul Kim, Daejeon (KR); Dong Hoon Baek, Daejeon (KR); Dong Geol Lee, Daejeon (KR); Ye Sung Yi, Daejeon (KR); Un Je Yang, Daejeon (KR)

(73) Assignees: KOREA ADVANCED INSTITUTE OF SCIENCE AND TECHNOLOGY, Daejeon (KR); EASYENDO SURGICAL, INC., Daejeon (KR)

( * ) Notice: Subject to any disclaimer, the term of this patent is extended or adjusted under 35 U.S.C. 154(b) by 43 days.

(21) Appl. No.: 17/056,763

(22) PCT Filed: Aug. 25, 2020

(86) PCT No.: PCT/KR2020/011310
§ 371 (c)(1),
(2) Date: Nov. 19, 2020

(87) PCT Pub. No.: WO2021/040376
PCT Pub. Date: Mar. 4, 2021

(65) Prior Publication Data
US 2021/0370529 A1    Dec. 2, 2021

(30) Foreign Application Priority Data

Aug. 29, 2019  (KR) .................. 10-2019-0106795
Aug. 24, 2020  (KR) .................. 10-2020-0106401

(51) Int. Cl.
*B25J 17/02* (2006.01)
*B25J 9/00* (2006.01)
(Continued)

(52) U.S. Cl.
CPC ......... *B25J 17/0266* (2013.01); *B25J 9/0015* (2013.01); *B25J 9/065* (2013.01); *B25J 9/104* (2013.01); *B25J 9/0078* (2013.01)

(58) Field of Classification Search
CPC ..... B25J 9/065; B25J 9/0015; A61B 1/00078; A61B 1/0053
See application file for complete search history.

(56) References Cited

U.S. PATENT DOCUMENTS

| 5,174,277 A * | 12/1992 | Matsumaru .......... A61B 1/0055 600/142 |
| 2011/0174108 A1* | 7/2011 | Graham ................. A61B 34/30 901/47 |
| 2015/0343649 A1 | 12/2015 | Galinson |

FOREIGN PATENT DOCUMENTS

| CN | 107433579 A * | 12/2017 | ............ B25J 9/0009 |
| EP | 165718 A * | 12/1985 | ........... A61B 1/0052 |

(Continued)

*Primary Examiner* — Daniel D Yabut
(74) *Attorney, Agent, or Firm* — JCIPRNET

(57) ABSTRACT

A flexible drive manipulator according to an example embodiment may include a proximal portion, a plurality of joint portions drivably connected from an end of the proximal portion with respect to a longitudinal axis, a distal portion connected to an end of the plurality of joint portions, a pair of drive wires passing through the plurality of joint portions in parallel along the longitudinal axis, the pair of drive wires configured to drive the plurality of joint portions in a rotational direction of rotation with respect to a transverse axis perpendicular to the longitudinal axis, and a fixing wire passing through the plurality of joint portions in a shape (Continued)

of converging along the longitudinal axis, the fixing wire configured to adjust rigidity of the plurality of joint portions.

7 Claims, 13 Drawing Sheets

(51) Int. Cl.
 *B25J 9/06* (2006.01)
 *B25J 9/10* (2006.01)

(56) References Cited

FOREIGN PATENT DOCUMENTS

| | | |
|---|---|---|
| JP | 2004337994 | 12/2004 |
| KR | 101369515 | 3/2014 |
| KR | 20190079790 | 7/2019 |
| WO | 2015093602 | 6/2015 |

* cited by examiner

FLEXIBLE DRIVE MANIPULATOR

TECHNICAL FIELD

The following description relates to a flexible drive manipulator.

BACKGROUND ART

A continuum manipulator includes a hyper-redundant manipulator in which multiple joints are continuously connected to form one manipulator with the number of degrees of freedom greater than the number of actuators, and a flexible manipulator in which one deformable body forms a manipulator to have an infinite number of degrees of freedom.

The continuum manipulator operates with a gradual curvature, unlike an manipulator formed of a single joint, and accordingly can be mainly used for medical equipment such as medical catheters, endoscopes, or surgical instruments that needs to be inserted along a flexible path, and industrial equipment such as water/sewer pipes, toilet aisles, engine interiors, switchboards, or the like that needs to enter a narrow and curved space.

As a method of driving the continuum manipulator, a position control method using a wire inserted along a longitudinal axis of a manipulator can be used, and in the case of using a wire driving method, redundant degrees of freedom are generated by the tension of a wire, which may cause a problem in forming a desired configuration. In addition, due to a structure in which a configuration is adjusted through the tension of the wire, there may be a problem in that the configuration can be easily deformed by an external force in a direction different from a direction of the wire.

In particular, when an operation is performed through an end effector of the continuum manipulator, since the continuum manipulator is continuously exposed to loads and torques in a transverse direction, there is a problem in that it is vulnerable to forming the desired configuration or maintaining the configuration.

Therefore, even if the continuum manipulator is driven by the wire driving method, there is an increasing need for a wire-driven continuum manipulator that is robust to loads and torques in a transverse direction without generating undesired redundant degrees of freedom.

The above-described background technology is possessed or acquired by the inventor in a derivation process of the present invention, and is not necessarily a known technology disclosed to the general public prior to filing of the present invention.

DISCLOSURE OF INVENTION

Technical Subject

An aspect provides a flexible drive manipulator.

Technical Solution

According to an aspect, there is a provided a flexible drive manipulator including a proximal portion, a plurality of joint portions drivably connected from an end of the proximal portion with respect to a longitudinal axis, a distal portion connected to an end of the plurality of joint portions, a pair of drive wires passing through the plurality of joint portions in parallel along the longitudinal axis, the pair of drive wires configured to drive the plurality of joint portions in a rotational direction of rotation with respect to a transverse axis perpendicular to the longitudinal axis, and a fixing wire passing through the plurality of joint portions in a shape of converging along the longitudinal axis, the fixing wire configured to adjust rigidity of the plurality of joint portions.

The joint portion may include a pair of contact portions in which both edge portions spaced along a transverse axis perpendicular to a central axis of the joint portion parallel with the longitudinal axis are formed to be recessed along the longitudinal axis, and a pair of fixing wire passages through which the fixing wire passes, the pair of fixing wire passages having an inclined shape so as to converge symmetrically to each other with respect to the longitudinal axis, and an interval between the pair of fixing wire passages of each of the joint portions may sequentially decrease as a joint portion among the plurality of joint portions is connected adjacent to the distal portion, and a portion of the fixing wire passing between the plurality of joint portions may be parallel with the longitudinal axis.

The fixing wire passage may include a front opening exposed toward the proximal portion, and a rear opening exposed toward the distal portion, and among a pair of joint portions connected adjacent to each other, the rear opening of a joint portion relatively adjacent to the proximal portion and the front opening of a joint portion relatively adjacent to the distal portion may be positioned on the same line parallel with the longitudinal axis.

A contact portion of each of a plurality of joint portions may rotate so as to be in close contact with an oppositely connected joint portion by a tensile force applied to the pair of drive wires, and among a pair of joint portions contacting adjacent to each other, the rear opening of a joint portion relatively adjacent to the proximal portion and the front opening of a joint portion relatively adjacent to the distal portion may be in close contact with each other so that shapes of respective openings are engaged with each other.

A portion of the fixing wire passing through the fixing wire passages of the plurality of joint portions may have an inclination of converging toward a central axis of each of the plurality of joint portions, and a portion of the fixing wire passing between the plurality of joint portions may be parallel with a central axis of a joint portion that has been previously passed through.

The flexible drive manipulator according to an aspect may further include a central wire passing through central axes of the plurality of joint portions, the central wire fixed to the distal portion, and the joint portion may further include a pair of drive wire passages formed to be spaced apart from each other along the transverse axis with respect to the central axis, the pair of drive wire passages through which the pair of drive wires pass, and a central wire passage through which the central wire passes along the central axis.

The pair of drive wire passages, the pair of fixing wire passages, and the central wire passage of the joint portion may be positioned on the same line along a traverse axis perpendicular to the central axis of the joint portion.

Effects

According to a flexible drive manipulator according to an example embodiment, it is possible to individually adjust driving and rigidity through two types of wire configurations of a drive wire and a fixing wire, and thus there is an advantage of being simple in terms of a structure and maintaining miniaturization.

According to the flexible drive manipulator according to an example embodiment, it is possible to adjust a tensile force applied to a fixing wire, thereby implementing variable rigidity.

According to the flexible drive manipulator according to an example embodiment, it is possible to prevent a flexion phenomenon that occurs due to redundant degrees of freedom when only a conventional flat wire is used.

According to the flexible drive manipulator according to an example embodiment, a fixing wire connected between both joint portions may maintain an angle between central axes of respective joint portions in an operation process that joint portions adjacent to each other are in rolling contact with each other, thereby preventing a magnitude and a direction of a tensile force formed for each section of the fixing wire from being dispersed, and a phenomenon of being caught between the joint portions.

BEST MODE FOR CARRYING OUT THE INVENTION

Figure 1:
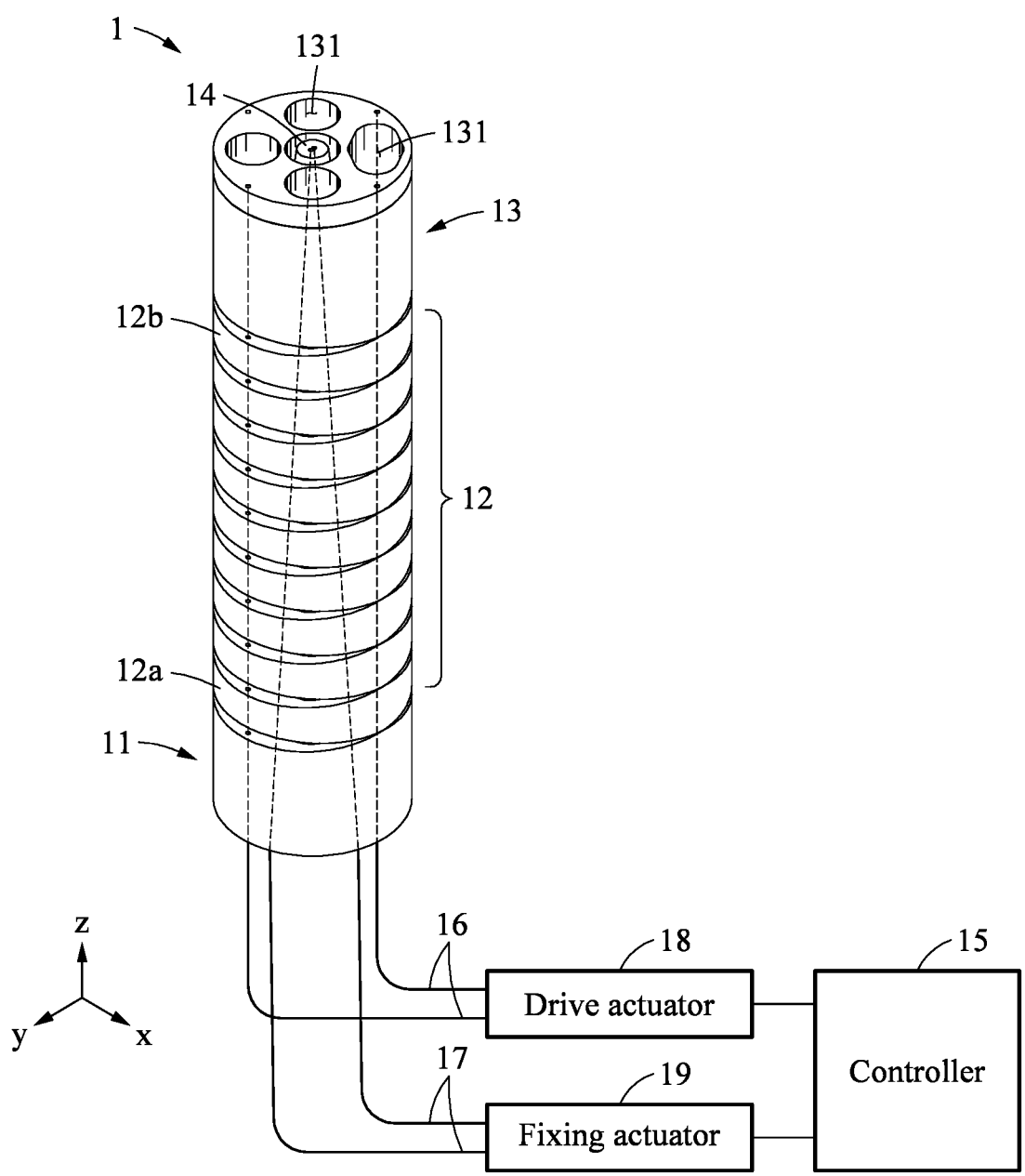
FIG. 1 is a perspective view of a flexible drive manipulator according to an example embodiment.

Hereinafter, example embodiments will be described in detail with reference to the illustrative drawings. Regarding reference numerals assigned to components in each drawing, it should be noted that the same components will be designated by the same reference numerals, wherever possible, even though they are illustrated in different drawings. Also, in the description of the example embodiments, detailed description of well-known related configurations or functions will be omitted when it is deemed that such description interferes with the understanding of the example embodiments.

In addition, terms such as first, second, A, B, (a), (b), and the like may be used herein to describe components of the example embodiments. These terms are only used to distinguish one component from another component, and essential, order, or sequence of corresponding components are not limited by these terms. It will be understood that when one component is referred to as being "connected to", "coupled to", or "linked to" another component, one component may be "connected to", "coupled to", or "linked to" another component via a further component although one component may be directly connected to or directly linked to another component.

A component included in any one example embodiment and another component including a function in common with that of the component will be described using the same designation in other example embodiments. Unless otherwise indicated, a description of one example embodiment may be applied to other example embodiments, and a detailed description will be omitted in an overlapping range.

Figure 2:
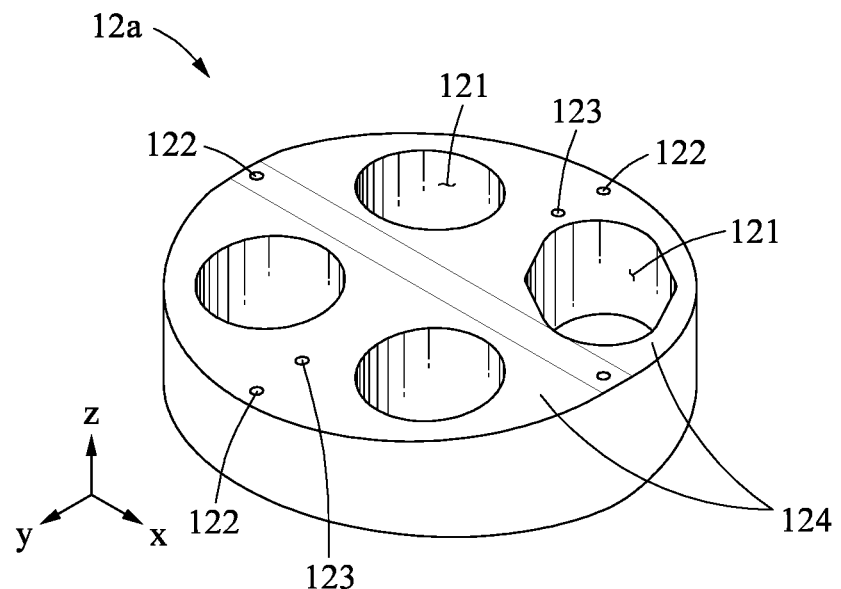
FIG. 2 is a perspective view of a joint portion according to an example embodiment.
Figure 3:
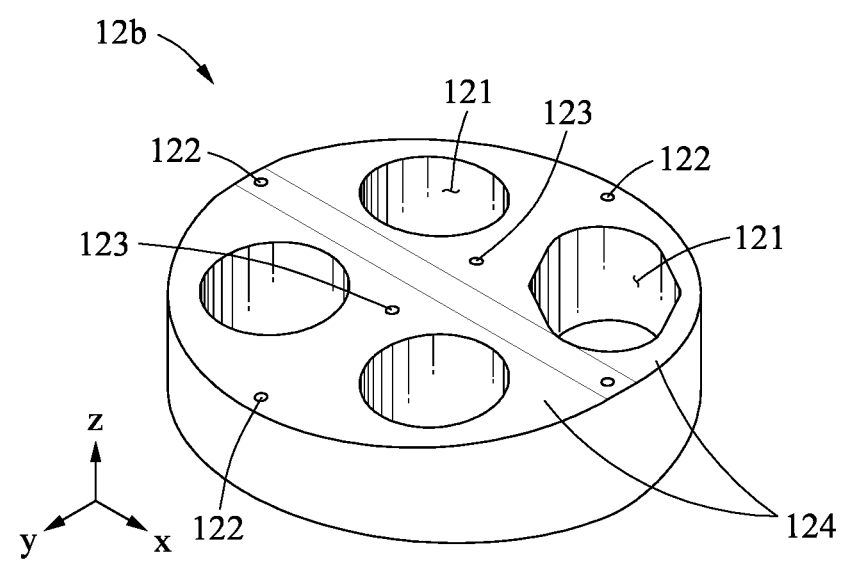
FIG. 3 is a perspective view of a joint portion according to an example embodiment.
Figure 4:
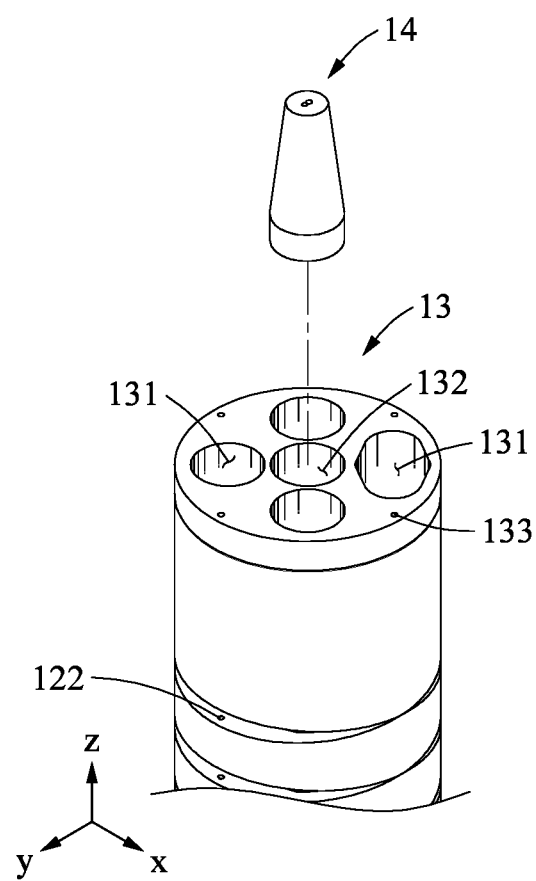
FIG. 4 is an exploded perspective view illustrating a coupling relationship between a distal portion and a wire gripping portion according to an example embodiment.
Figure 5:
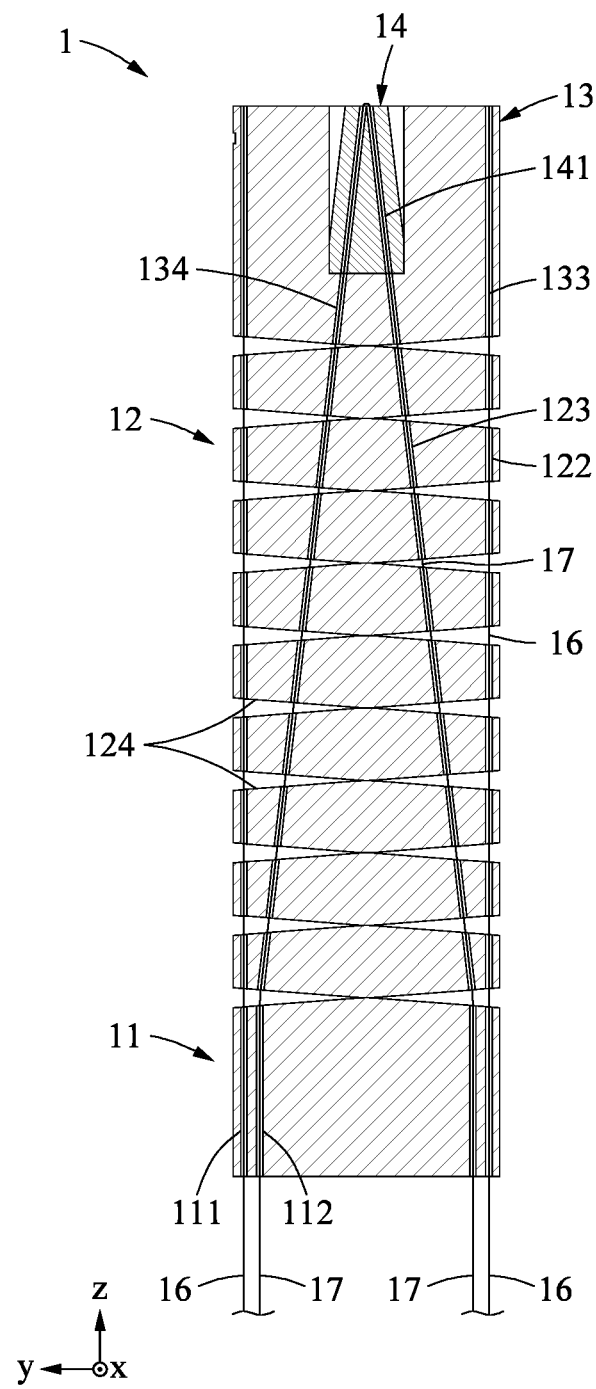
FIG. 5 is a cross-sectional view of a flexible drive manipulator according to an example embodiment.
Figure 6:
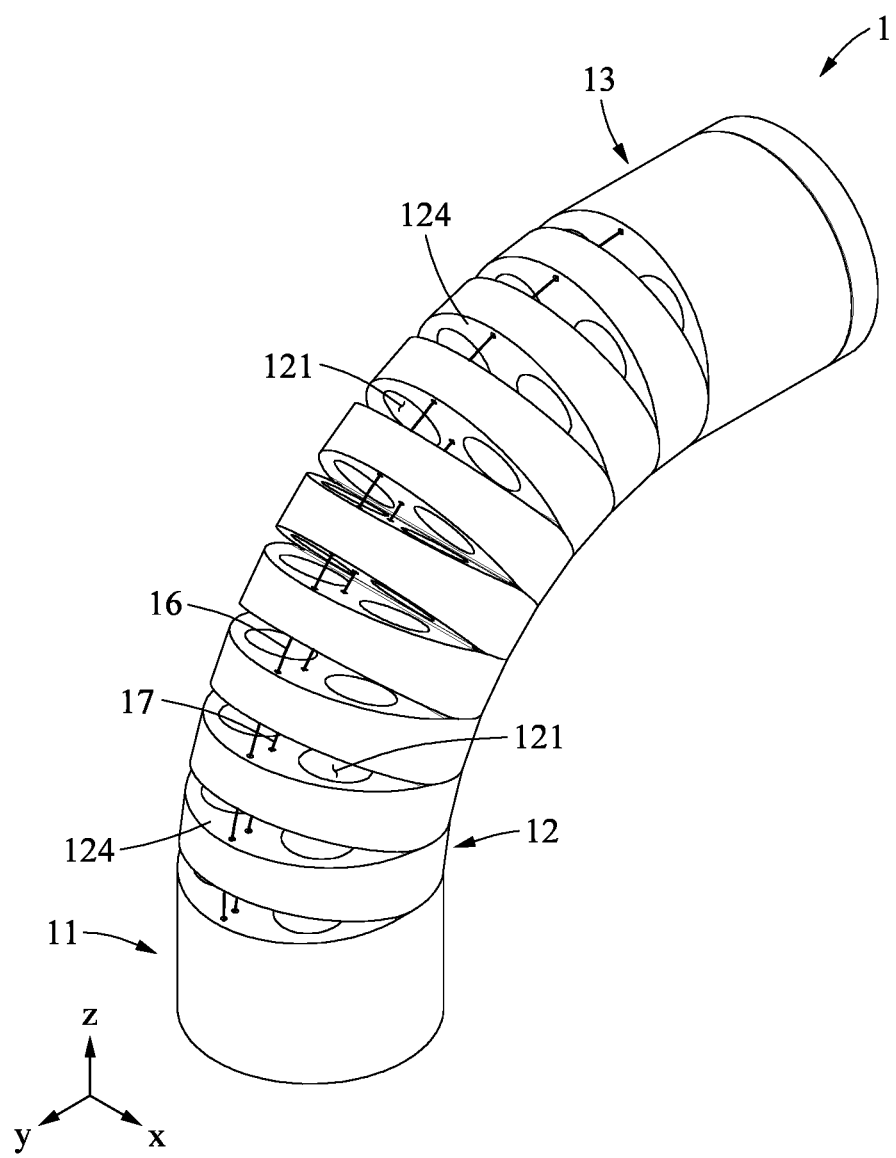
FIG. 6 is a perspective view illustrating a state in which a flexible drive manipulator is driven in one direction according to an example embodiment.
Figure 7:
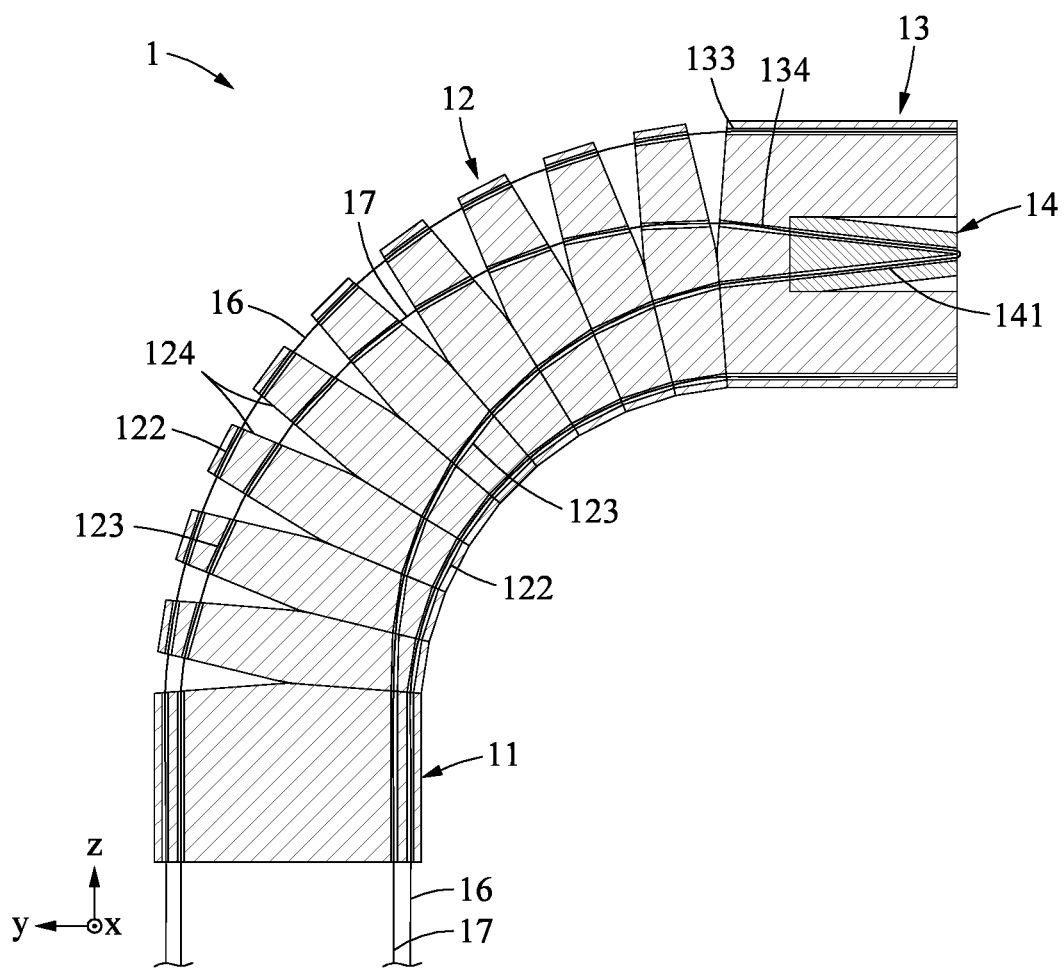
FIG. 7 is a cross-sectional view illustrating a state in which a flexible drive manipulator is driven in one direction according to an example embodiment.

FIG. 1 is a perspective view of a flexible drive manipulator according to an example embodiment, FIG. 2 is a perspective view of a joint portion according to an example embodiment, FIG. 3 is a perspective view of a joint portion according to an example embodiment, FIG. 4 is an exploded perspective view illustrating a coupling relationship between a distal portion and a wire gripping portion according to an example embodiment, FIG. 5 is a cross-sectional view of a flexible drive manipulator according to an example embodiment, FIG. 6 is a perspective view illustrating a state in which a flexible drive manipulator is driven in one direction according to an example embodiment, and FIG. 7 is a cross-sectional view illustrating a state in which a flexible drive manipulator is driven in one direction according to an example embodiment.

Referring to FIGS. 1 to 7, a flexible drive manipulator 1 according to an example embodiment is a continuum manipulator that operates through the tension of a wire.

For example, the flexible drive manipulator 1 has an elongated shape along a longitudinal axis (z-axis in the drawing) based on a state in which a tensile force is not applied to a drive wire 16, that is, a neutral state that is not driven.

Hereinafter, in the description of a configuration of the flexible drive manipulator 1, it should be noted that it will be described based on a non-driving state as illustrated in FIG. 1, unless otherwise indicated.

The flexible drive manipulator 1 according to an example embodiment may include a proximal portion 11 serving as a reference for driving, a plurality of joint portions 12 drivably connected from an end of the proximal portion 11 with respect to a longitudinal axis, a distal portion 13 connected to an end of the plurality of joint portions 12, a drive wire 16 passing through the plurality of joint portions 12 in parallel along the longitudinal axis to drive the plurality of joint portions 12 in a rotational direction with respect to an axis perpendicular to the longitudinal axis, a fixing wire 17 passing through the plurality of joint portions 12 in a shape of converging along the longitudinal axis to adjust rigidity of the plurality of joint portions 12, a drive actuator 18 connected to the drive wire 16 to adjust a tensile force of the drive wire 16, a fixing actuator 19 connected to the fixing wire 17 to adjust a tensile force of the fixing wire 17, and a controller 15 configured to control the drive actuator 18 and the fixing actuator 19.

The proximal portion 11 may be a member that serves as a relative reference for a rotational motion in a rotational direction in which the plurality of joint portions 12 are rotated with respect to an axis (y-axis or x-axis in the drawing) perpendicular to the longitudinal axis (z-axis in the drawing). For example, a central axis of the proximal portion 11 may have a fixed position so as to correspond to the longitudinal axis.

For example, the proximal portion 11 may include a drive wire inlet passage 111 through which the drive wire 16 passes along the longitudinal axis and a fixing wire inlet passage 112 through which the fixing wire 17 passes.

For example, the drive wire inlet passage 111 may be a pair of passages formed through both edge portions spaced apart from the central axis of the proximal portion 11 along the rotational direction as illustrated in FIG. 5. In other words, the drive wire inlet passage 111 may be formed at a position spaced apart with respect to the longitudinal axis of the flexible drive manipulator 1.

For example, the fixing wire inlet passage 112 may be formed as a pair of passages formed through a portion spaced apart side by side from the central axis of the proximal portion 11 along a direction perpendicular to the longitudinal axis as illustrated in FIG. 5. In other words, the fixing wire inlet passage 112 may be formed at a position spaced apart at intervals that are symmetrical with respect to the longitudinal axis of the flexible drive manipulator 1.

For example, a pair of fixing wire inlet passages 112 may be formed inside from the pair of drive wire inlet passages 111, respectively. In other words, with respect to the longitudinal axis of the flexible drive manipulator 1, the fixing wire inlet passage 112 may be formed at a position closer than that of the drive wire inlet passage 111.

The plurality of joint portions 12 may be a set of a plurality of continua continuously connected from the proximal portion 11 through the drive wire 16 and the fixing wire 17.

For example, the plurality of joint portions 12 may perform flexion or extension motions on the proximal portion 11 in the rotational direction with respect to the axis perpendicular to the longitudinal axis.

For example, the plurality of joint portions 12 each may have different angles with respect to the joint portions 12 adjacent to each other. For example, the plurality of joint portions 12 may be connected in at least one of a rolling contact manner, a gear manner, and a hinge manner.

In the following description, a case in which the plurality of joint portions 12 are connected in a rolling contact manner is exemplarily described, but it should be noted that it is not necessarily limited thereto.

For example, a joint portion 12 most adjacent to the proximal portion 11 among the plurality of joint portion 12 may be referred to as a proximal joint portion 12a, and a joint portion 12 most adjacent to the distal portion 13 may be referred to as a distal joint portion 12b.

For example, each joint portion 12 may include a pair of contact portions 124, a pair of drive wire passages 122, a pair of fixing wire passages 123, and an internal passage 121.

When the joint portions 12 adjacent to each other are bent by a particular angle or more, the contact portions 124 formed on respective joint portions 12 may be in contact with each other, thereby limiting a flexion angle. The contact portion 124 may have a recessed shape so as to allow a relative angle change between the joint portions 12 adjacent to each other. On the basis of a case in which the flexible drive manipulator 1 is in a neutral configuration as illustrated in FIG. 1, on one side of one joint portion 12 facing the other adjacent joint portion 12, a protrusion height of the contact portion 124 is formed lower than that of a portion that is in contact with the other adjacent joint portion 12.

According to the pair of contact portions 124, an angle at which respective joint portions 12 are connected to each other may be changed so that the plurality of joint portions 12 are bent toward the rotational direction as illustrated in FIGS. 6 and 7, and thus the configuration of the flexible drive manipulator 1 may be changed.

For example, the pair of contact portions 124 may be formed on both surfaces facing the adjacent joint portions 12 along the longitudinal axis as illustrated in FIG. 5, but it should be noted that the pair of contact portions 124 may be formed only on one surface.

The pair of drive wire passages 122 may be formed in an edge portion of each of the pair of contact portions 124 along a direction perpendicular to the central axis of the joint portion 12, and the drive wire 16 may pass therethrough.

For example, on the basis of a neutral state in which the plurality of joint portions 12 are not bent as illustrated in FIGS. 3 to 5, the pair of drive wire passages 122 formed in each of the plurality of joint portions 12 are parallel with the longitudinal axis, and have positions that overlap each other along a direction parallel with the longitudinal axis.

The pair of fixing wire passages 123 may be a pair of passages formed through a portion spaced apart side by side from the central axis of the proximal portion 11 along the direction perpendicular to the central axis of the joint portion 12. For example, the pair of fixing wire passages 123 may have a structure of being symmetrical with respect to the central axis of the joint portion 12.

For example, the pair of fixing wire passages 123 may have an inclined shape so as to converge to the central axis of the joint portion 12 toward a distal direction.

For example, the pair of fixing wire passages 123 formed in each of the plurality of joint portions 12 may be formed at a position relatively adjacent to the central axis of the joint portion 12 toward the joint portion 12 adjacent to the distal portion 13 from the proximal portion 11.

In other words, as illustrated in FIG. 5, an interval between the pair of fixing wire passages 123 of the plurality of joint portions 12 may sequentially decrease along the longitudinal axis, and at the same time, the pair of fixing wires passages 123 of each of the plurality of joint portions 12 may form an oblique inclination in a shape of converging with each other along the longitudinal axis.

For example, in the case of the proximal joint portion 12a illustrated in FIG. 2, it can be confirmed that the pair of fixing wire passages 123 are formed at positions close to the pair of drive wire passages 122, respectively. Conversely, in the case of the distal joint portion 12b illustrated in FIG. 3, it can be confirmed that the pair of fixing wire passages 123 are respectively formed at positions spaced apart inwardly from the pair of drive wire passages 122.

According to the pair of fixing wire passages 123 having a shape of converging toward the central axis of the joint portion 12 as a distance from the proximal portion 11 increases, the fixing wire 17 passing through the plurality of joint portions 12 as illustrated in FIG. 5 may pass in a shape of converging toward a center as a distance to the longitudinal axis decreases.

For example, as illustrated in the drawings, based on a center of the joint portion 12, the fixing wire passage 123 and the drive wire passage 122 may be positioned in the same radial direction. According to the above-structure, lateral rigidity may be improved more efficiently.

Unlike the above-structure, the fixing wire passage 123 and the drive wire passage 122 may not be positioned in the same radial direction, and unless otherwise indicated, it should be noted that the scope of the present invention is not necessarily limited to being positioned in the same radial direction.

The internal passage 121 may be formed to be penetrated along the longitudinal axis. For example, various end effectors depending on the purpose, including surgical instruments such as a camera, forceps or laser, may be inserted into the internal passage 121 from the proximal portion 11 toward the distal portion 13, and at the same time, a channel through which a cable or wire for manipulating and driving the surgical instruments passes may be formed.

For example, the internal passage 121 may be formed in plural numbers. In this case, when viewed from the longitudinal axis, the plurality of internal passages 121 may be formed at a position that does not overlap a virtual straight line connecting the pair of drive wire passages 122 and the pair of fixing wire passages 123 along an axis perpendicular to the central axis.

The distal portion 13, which is a member corresponding to a drive end of the plurality of joint portions 12, may be connected to the distal joint portion 12b that is connected in a last order from the proximal portion 11 among the plurality of joint portions 12.

As illustrated, the distal portion 13 may form a distal end of the flexible drive manipulator 1, but it should be noted that the proximal portion 11 and the distal portion 13 described herein are merely configurations for giving a relative positional relationship between members connected to the plurality of joint portions 12, and a structure in which each of the proximal portion 11 and the distal portion 13 is connected to an additional external component or a plurality of flexible drive manipulators 1 are connected in series is possible.

For example, the distal portion 13 may include a pair of drive wire receiving holes 133, a pair of fixing wire receiving holes 134, a central groove 132, a wire gripping portion 14, and an internal passage 131.

The pair of drive wire receiving holes 133 may be a pair of holes into which the drive wire 16 passing through the plurality of joint portions 12 is inserted along the longitudinal axis.

For example, as illustrated in FIG. 5, when viewed from the longitudinal axis, the pair of drive wire receiving holes 133 may be formed at positions that overlap the pair of drive wire passages 122 formed in the plurality of joint portion 12.

For example, ends of the drive wires 16 formed as a pair as illustrated in FIG. 5 may be inserted into and fixed to the pair of drive wire receiving holes 133, respectively.

As another example, it should be noted that the pair of drive wire receiving holes 133 may be formed as one passage in which the pair of drive wire receiving holes 133 communicate with each other, and accordingly one fixing wire 17 may sequentially pass therethrough, and as a result, it is possible to form a structure in which the fixing wire 17 circulates through the flexible drive manipulator 1.

The drive wire 16 passing through the plurality of joint portions 12 may be inserted into the pair of fixing wire receiving holes 134.

For example, the pair of fixing wire receiving holes 134 may be formed in a portion spaced apart side by side from the central axis of the distal portion 13 along the direction perpendicular to the longitudinal axis.

For example, the pair of fixing wire receiving holes 134 may form a passage having a convergent shape while having the same angle as those of the pair of fixing wire passages 123 so as to correspond to the pair of fixing wire passages 123 of the plurality of joint portions 12 having a shape of converging along the longitudinal axis.

In the central groove 132, the wire gripping portion 14 may be accommodated in the distal portion 13. For example, the central groove 132 may be formed in a center of the distal portion 13 to communicate with the pair of fixing wire receiving holes 134.

For example, the central groove 132 may be a groove formed to be recessed from an upper side with respect to the longitudinal axis as illustrated in FIG. 4. Accordingly, the wire gripping portion 14 may be detachably inserted from an upper side of the distal portion 13.

As illustrated in FIG. 5, the central groove 132 may communicate with the pair of fixing wire receiving holes 134 from a lower side with respect to the longitudinal axis.

The wire gripping portion 14 may grip the fixing wire 17 that is inserted into the central groove 132 to be inserted into the distal portion 13.

For example, the wire gripping portion 14 may be formed of a material that is relatively more flexible than that of the distal portion 13. For example, the wire gripping portion 14 may include a conical shape with a cross-sectional width decreasing toward the longitudinal axis.

For example, the wire gripping portion 14 may include a fixing passage 141 through which the fixing wire 17 passes.

The fixing passage 141 may form a passage having a convergent shape while having the same angle as those of the pair of fixing wire passages 123 and the pair of fixing wire receiving holes 134 so as to correspond to the pair of fixing wire passages 123 of the plurality of joint portions 12 having a shape of converging along the longitudinal axis.

For example, the fixing passage 141 may communicate with the pair of fixing wire receiving holes 134 while facing each other at an accurate position and angle as illustrated in FIG. 5.

For example, the fixing wire 17 passing through the fixing passage 141 may be exposed to an upper side of the wire gripping portion 14 as illustrated in FIG. 5, and the fixing wire 17 may be branched into both sides along a transverse direction perpendicular to the central axis of each joint portion 12 starting from the exposed point to pass through the plurality of joint portions 12.

For example, the fixing passage 141 may be formed as a pair of passages passing through the wire gripping portion 14, but may be formed as one passage passing through the interior of the fixing passage 141.

According to the above-structure, even though a sudden tensile force is formed in the fixing wire 17 or a tensile force formed in each of the fixing wires 17 branched into two strands along the transverse direction perpendicular to the central axis is formed unbalanced when the flexible drive manipulator 1 is bent along one direction as illustrated in FIG. 7, the wire gripping portion 14 may have flexibility and margin to allow a shape of the fixing wire 17 to be changeable within the central groove 132, thereby reducing possibilities of damage caused by sudden driving of the wires 16 and 17 and damage of the wires 16 and 17 themselves.

The internal passage 131 may be a passage formed through the distal portion 13 along the longitudinal axis. When viewed from the longitudinal axis, the internal passage 121 of the plurality of joint portions 12 and the internal passage 131 of the distal portion 13 may overlap each other. Therefore, a surgical instrument inserted through the internal passage 121 of the plurality of joint portions 12 may be supplied through the internal passage 131 of the distal portion 13 in a distal direction.

One end of the drive wire 16 may be connected to the drive actuator 18, and the other end of the drive wire 16 may be fixed to the distal portion 13 after sequentially passing through the proximal portion 11 and the plurality of joint portions 12. For example, the drive wire 16 may be formed as a pair of wires spaced apart from each other and extending while facing each other along the direction perpendicular to the longitudinal axis.

For example, a pair of drive wires 16 may be inserted into the pair of drive wire inlet passages 111 of the proximal portion 11, the pair of drive wire passages 122 of the plurality of joint portions 12, and the pair of drive wire receiving holes 133 of the distal portion 13, respectively.

According to the above-structure, on the basis of the neutral state in which the flexible drive manipulator 1 is not driven as illustrated in FIG. 5, the pair of drive wires 16 passing through opposite edge portions of the flexible drive manipulator 1 may extend in a state of being parallel with each other toward the longitudinal axis.

One end of the fixing wire 17 may be connected to the fixing actuator 19, and the other end of the fixing wire 17 may be fixed to the distal portion 13 after sequentially passing through the proximal portion 11 and the plurality of joint portions 12 in a convergent shape. For example, the fixing wire 17 may have a structure of a wire passing through the proximal portion 11 and the plurality of joint portions 12 in a state of being spaced apart side by side along the transverse direction perpendicular to the central axis, and two strands of the fixing wire 17 may be connected to each other in the distal portion 13.

For example, the two strands of the fixing wire 17 may be connected to each other in the fixing passage 141 of the wire gripping portion 14 after passing through the pair of fixing wire inlet passages 112 of the proximal portion 11, the pair of fixing wire passages 123 of the plurality of joint portions 12, and the pair of fixing wire receiving holes 134 of the distal portion 13.

In other words, after passing through the fixing wire passages 123 formed on one side with respect to the transverse direction perpendicular to central axes of the pair of fixing wire passages 123, one fixing wire 17 may pass through the fixing wire passages 123 on the other side which are not passed through by changing a direction while passing through the fixing passage 141 of the wire gripping portion 14, and as a result, may have a structure in which both ends protrude in a proximal direction to be connected to the fixing actuator 19.

As another example, the two strands of the fixing wire 17 may be formed as a pair of wires that each connect between the fixing actuator 19 and the wire gripping portion 14 along an independent path without being connected to each other.

According to the above-structure, on the basis of the neutral state in which the flexible drive manipulator 1 is not driven as illustrated in FIG. 5, the two strands of the fixing wire 17 having both ends connected to the fixing actuator 19 may have a structure of converging symmetrically so as to have an oblique angle toward each other while passing through the plurality of joint portions 12.

The drive actuator 18 may be connected to each of the pair of drive wires 16 to apply a tensile force to each drive wire 16.

The fixing actuator 19 may be connected to both ends of the fixing wire 17 circulating and passing through the plurality of joint portions 12 and the distal portion 13 to apply a tensile force to the fixing wire 17.

The controller 15 may drive the plurality of joint portions 12 by adjusting the tensile force applied to the drive wire 16 through the drive actuator 18.

For example, the controller 15 may apply a relatively large tensile force to one of the pair of drive wires 16 passing through the pair of drive wire passages 122 of each of the plurality of joint portions 12 in a state of being spaced apart side by side along the transverse direction perpendicular to the central axis of each of the plurality of joint portions 12, and thereby the plurality of joint portions 12 may perform a flexion motion toward one direction of rotational directions as illustrated in FIGS. 6 and 7.

The controller 15 may adjust rigidity of maintaining a driving configuration of the plurality of joint portions 12 by adjusting the tensile force applied to the fixing wire 17 through the fixing actuator 19.

According to the flexible drive manipulator 1 according to an example embodiment, a joint structure that is robust to a lateral load and a torque may be provided.

When using only wires that are inserted in a state of being spaced apart in parallel with each other along the longitudinal axis in a continuum manipulator, it is vulnerable to a load in the traverse direction perpendicular to the longitudinal axis, and accordingly there may be a problem in that redundant degrees of freedom may be easily generated by an external force and self-weight, or a configuration may be easily collapsed.

However, the flexible drive manipulator 1 according to an example embodiment may include the fixing wire 17 having a shape of converging toward an end thereof in addition to the drive wire 16 parallel with the longitudinal axis, thereby improving rigidity against the lateral load that cannot be supported by only the pair of drive wires 16 inserted in parallel.

According to the flexible drive manipulator 1 according to an example embodiment, a tensile force may be applied to the fixing wire 17 even in the neutral state in which the plurality of joint portions 12 are not bent as illustrated in FIG. 5, thereby improving rigidity so that the plurality of joint portions 12 are maintained in an extended state even though a lateral load and a torque are generated.

Similarly, a tensile force may be applied to the fixing wire 17 even in a state in which the plurality of joint portions 12 are bent through the tension of the drive wire 16 as illustrated in FIGS. 6 and 7, improving rigidity so that the plurality of joint portions 12 maintain a bent configuration even though a lateral load and a torque are generated.

In addition, according to the fixing wire 17, it is possible to easily align a neutral axis (that is, the longitudinal axis of the flexible drive manipulator 1) between the plurality of joint portions 12, thereby preventing a problem in which redundant degrees of freedom are generated by asymmetry of each of the plurality of joint portions 12.

Figure 8:
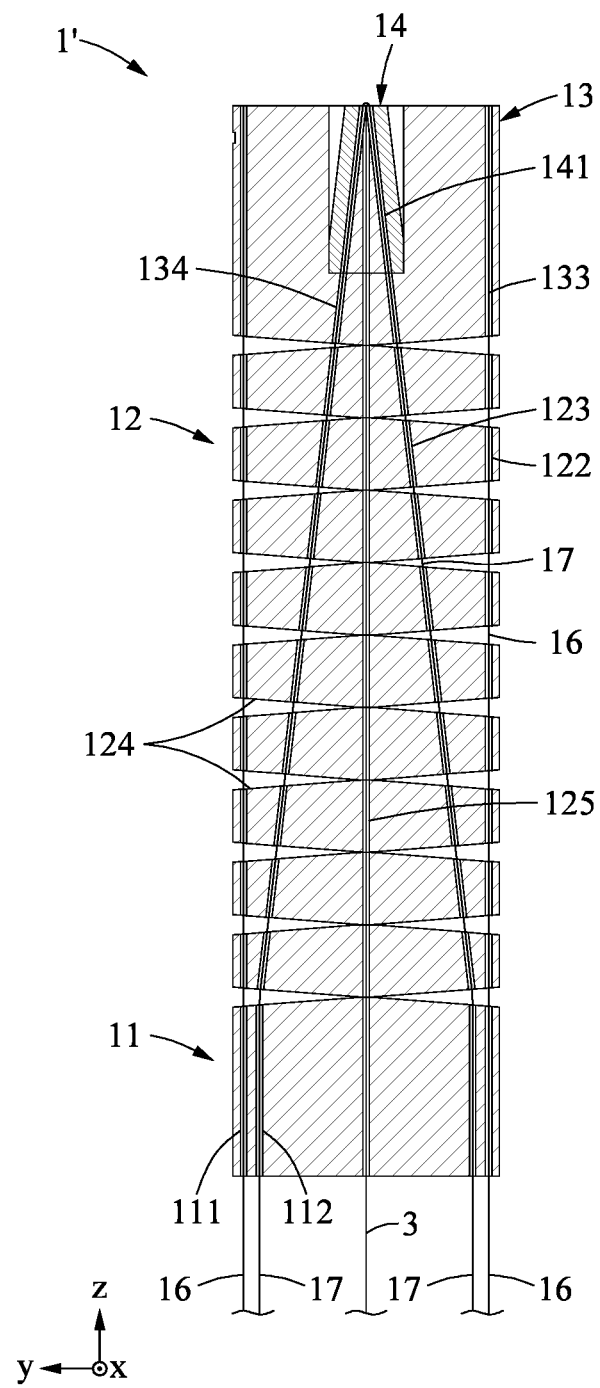
FIG. 8 is a cross-sectional view of a flexible drive manipulator according to an example embodiment.

FIG. 8 is a cross-sectional view of a flexible drive manipulator according to an example embodiment.

Referring to FIG. 8, a configuration of a flexible drive manipulator 1' having a configuration different from those of the example embodiments illustrated in FIGS. 1 to 7 can be confirmed.

It can be understood that the flexible drive manipulator 1' according to an example embodiment additionally has a configuration of a central wire 3 passing through a part of the center in the flexible drive manipulator 1 of FIGS. 1 to 7.

For example, the flexible drive manipulator 1' may include a proximal portion 11 serving as a reference for driving, a plurality of joint portions 12 drivably connected from an end of the proximal portion 11 with respect to a longitudinal axis, a distal portion 13 connected to an end of the plurality of joint portions 12, a drive wire 16 passing through the plurality of joint portions 12 in parallel along the longitudinal axis to drive the plurality of joint portions 12 in a rotational direction with respect to an axis perpendicular to the longitudinal axis, a fixing wire 17 passing through the plurality of joint portions 12 in a shape of converging along the longitudinal axis to adjust rigidity of the plurality of joint portions 12, a central wire 3 passing through centers of the plurality of joint portions 12 along the longitudinal axis to be fixed to the distal portion 13, a drive actuator 18 connected to the drive wire 16 to adjust a tensile force of the drive wire 16, a fixing actuator 19 connected to the fixing wire 17 to adjust a tensile force of the fixing wire 17, and a controller 15 configured to control the drive actuator 18 and the fixing actuator 19.

On the basis of the neutral state in which the plurality of joint portions 12 are not driven as illustrated in FIG. 8, the central wire 3 may be fixed to the distal portion 13 after passing through along neutral axes of the plurality of joint portions 12. For example, the central wire 3 may be connected to a wire gripping portion 14 to be fixed thereto. Although not illustrated, it should be noted that a tensile force of the central wire 3 may be adjusted and an auxiliary actuator that can be controlled through the controller 15 may be additionally provided.

As the central wire 3 has a configuration of passing through the centers of the plurality of joint portions 12, each of the plurality of joint portions 12 may further include a central wire passage 125 formed through a central portion along the longitudinal axis so that the central wire 3 passes therethrough.

According to the central wire 3 passing through the neutral axis of each of the plurality of joint portions 12, the neutral axis of each of the plurality of joint portions 12 may be stably aligned. Thus, it is possible to prevent a problem in which redundant degrees of freedom are generated by asymmetry of each of the plurality of joint portions 12.

Figure 9:
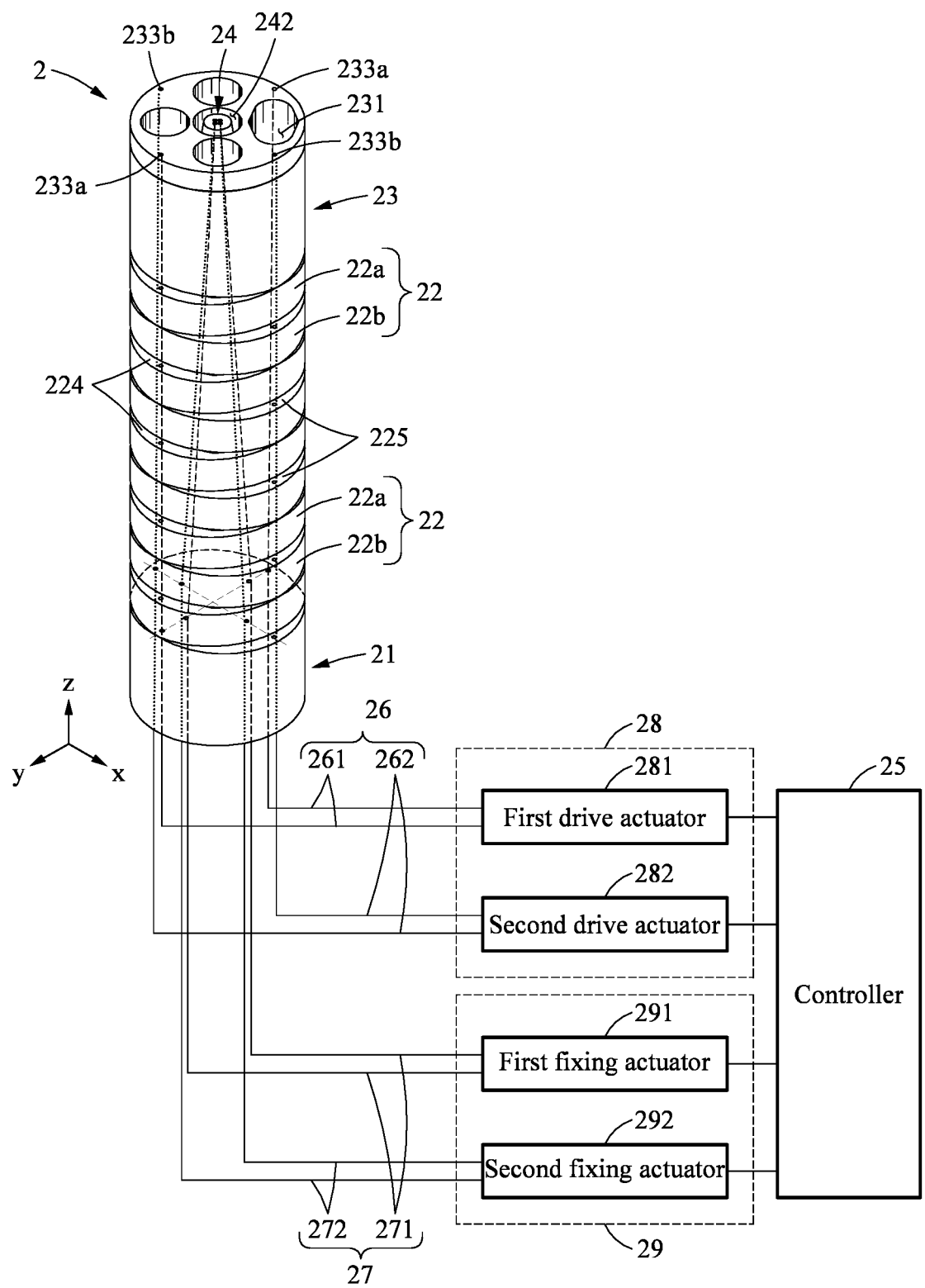
FIG. 9 is a perspective view of a flexible drive manipulator according to an example embodiment.
Figure 10:
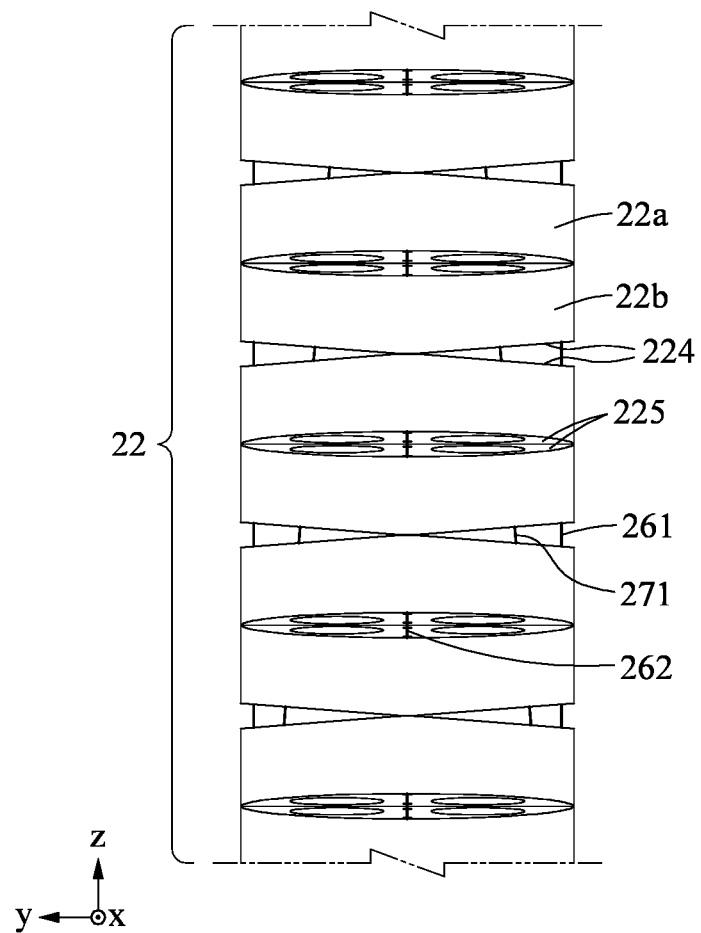
FIG. 10 is a front view of a flexible drive manipulator according to an example embodiment.
Figure 11:
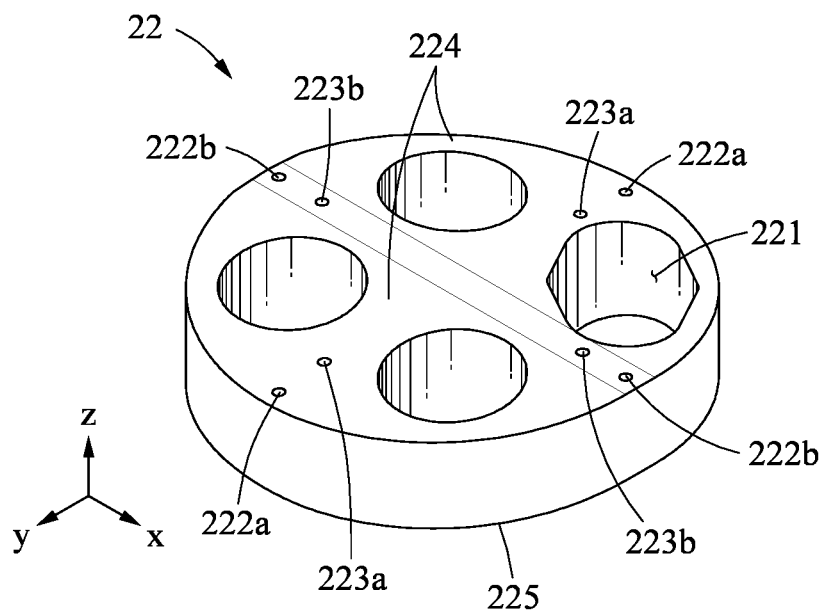
FIG. 11 is a perspective view of a joint portion according to an example embodiment.
Figure 12:
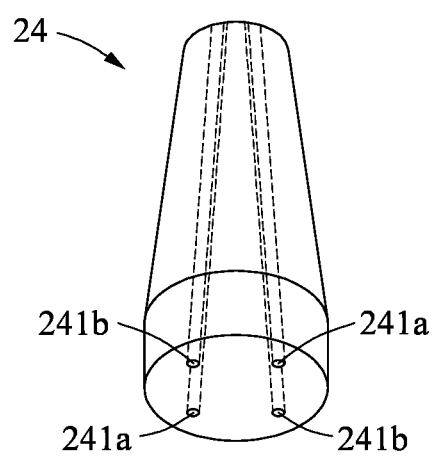
FIG. 12 is a bottom perspective view of a wire gripping portion according to an example embodiment.

FIG. 9 is a perspective view of a flexible drive manipulator according to an example embodiment, FIG. 10 is a front view of a flexible drive manipulator according to an example embodiment, FIG. 11 is a perspective view of a joint portion according to an example embodiment, and FIG. 12 is a bottom perspective view of a wire gripping portion according to an example embodiment.

Referring to FIGS. 9 to 12, a configuration of a flexible drive manipulator 2 having a configuration different from those of the example embodiments illustrated in FIGS. 1 to 7 can be confirmed.

It can be understood that the flexible drive manipulator 2 according to an example embodiment has a configuration of a joint portion and a configuration of a wire that are added thereto or are modified so as to allow the flexible drive manipulator 1 using a one degree of freedom driving method illustrated in FIGS. 1 to 7 to be driven with two degrees of freedom.

The flexible drive manipulator 2 according to an example embodiment may include a proximal portion 21, a plurality of joint portions 22, a distal portion 23, a first drive wire 261, a second drive wire 262, a first fixing wire 271, a second fixing wire 272, a drive operator 28, a fixing operator 29, and a controller 25.

The proximal portion 21 may be a member serving as a relative reference for driving in a first rotational direction in which the plurality of joint portions 22 rotate with respect to a first transverse axis (x-axis in the drawing) perpendicular to a longitudinal axis and a second rotational direction in which the plurality of joint portions 22 rotate with respect to a second transverse axis (y-axis in the drawing) perpendicular to the first transverse axis.

The plurality of joint portions 22 may be a set of a plurality of continua continuously connected from the proximal portion 21 through the first drive wire 261, the second drive wire 262, the first fixing wire 271, and the second fixing wire 272.

For example, the plurality of joint portions 22 may perform flexion or extension motions on the proximal portion 21 with two degrees of freedom along the first and second rotation directions.

For example, the plurality of joint portions 22 may include a portion in which two types of joint portions 22 are alternately arranged with each other according to an order of being connected from the proximal portion 21. For example, the plurality of joint portions 22 may be divided into a first joint portion 22a and a second joint portion 22b according to a type.

For example, the first joint portion 22a and the second joint portion 22b may be distinguished according to an angle at which the joint portion 22 having the same shape is rotated with respect to a central axis parallel with a longitudinal axis. For example, when the angle is 0 degrees, it may be referred to as the first joint portion 22a, and when the angle is 90 degrees, it may be referred to as the second joint portion 22b. It should be noted that a description of each of the first joint portion 22a and the second joint portion 22b will be replaced with a description of one joint portion 22 below.

For example, the joint portion 22 may include a pair of first contact portions 224, a pair of second contact portions 225, a pair of first drive wire passages 222a, a pair of second drive wire passages 222b, a pair of first fixing wire passages 223a, a pair of second fixing wire passages 223b, and an internal passage 221.

The pair of first contact portions 224 may be formed on one surface of both surfaces of the joint portion 22. The pair of first contact portions 224 may be formed in directions opposite to each other with respect to a first virtual line (y-axis in the drawing) perpendicular to the central axis of the joint portion 22.

The pair of first contact portions 224 may have a protrusion height lower than a maximum protrusion height of a portion of the one surface corresponding to the first virtual line.

For example, as illustrated in FIGS. 10 and 11, the pair of first contact portions 224 may be a portion in which a surface portion of any one of both surfaces facing the joint portions 22 adjacent to each other is recessed in a longitudinal direction toward both edges along a direction (y-axis direction) perpendicular to the central axis.

The pair of second contact portions 225 may be formed on the other surface of the both surfaces of the joint portion 22. The pair of second contact portions 225 may be formed in directions opposite to each other with respect to a second virtual line that is simultaneously perpendicular to the central axis of the joint portion 22 and the first virtual line.

The pair of second contact portions 225 may have a protrusion height lower than a maximum protrusion height of a portion of the other surface corresponding to the second virtual line.

For example, as illustrated in FIGS. 10 and 11, the pair of second contact portions 225 may be a portion in which a surface portion of the other of the both surfaces facing the joint portions 22 adjacent to each other is recessed in the longitudinal direction toward the both edges along a direction (x-axis direction) perpendicular to the central axis.

For example, as illustrated in FIG. 10, the first joint portion 22a may have a first contact portion 224 formed on an upper surface thereof and a second contact portion 225 formed on a lower surface thereof. Conversely, the second joint portion 22b may have the second contact portion 225 formed on an upper surface thereof and the first contact portion 224 formed on a lower surface thereof.

According to the above-structure, the second joint portion 22b positioned more adjacent to an upper side than the first joint portion 22a may perform a flexion motion in the first rotational direction (rotational direction with respect to the x-axis) perpendicular to the longitudinal axis, and the first joint portion 22a positioned more adjacent to the upper side than the second joint portion 22b may perform a flexion motion in the second rotational direction (rotational direction with respect to the y-axis).

As a result, as the first joint portion 22a and the second joint portion 22b are alternately connected, the plurality of joint portions 22 may be driven with two degrees of freedom in the first and second rotational directions.

The first drive wire passage 222a may be formed at an edge portion of the first contact portion 224 to allow the first drive wire 261 to pass therethrough.

The second drive wire passage 222b may be formed at an edge portion of the second contact portion 225 to allow the second drive wire 262 to pass therethrough.

For example, the pair of first drive wire passages 222a and the pair of second drive wire passages 222b may be formed at positions spaced apart at an angle perpendicular to each other radially along an edge periphery of the joint portion 22 as illustrated in FIG. 11.

The first fixing wire passage 223a may be formed in the first contact portion 224 to allow the first fixing wire 271 to pass therethrough. For example, the pair of first fixing wire passages 223a may be respectively formed through at points spaced apart inwardly from the pair of first drive wire passages 222a along the first virtual line perpendicular to the central axis.

The second fixing wire passage 223b may be formed in the second contact portion 225 to allow the second fixing wire 272 to pass therethrough. For example, the pair of second fixing wire passages 223b may be respectively formed through at points spaced apart inwardly from the pair of second drive wire passages 222b along the second virtual line perpendicular to the central axis and the first virtual line.

For example, the pair of first fixing wire passages 223a and the pair of second fixing wire passages 223b each may have a shape of obliquely converging inwardly in an order of a distance from the proximal portion 21 increasing. For example, the pair of first fixing wire passages 223a and the pair of second fixing wire passages 223b may be formed at positions spaced apart at an angle perpendicular to each other radially along the periphery of the joint portion 22 as illustrated in FIG. 11.

The distal portion 23, which is a member corresponding to a drive end of the plurality of joint portions 22, may be connected to the joint portion 22 that is connected in a last order from the proximal portion 21 among the plurality of joint portions 22.

For example, the distal portion 23 may include the pair of first drive wire receiving holes 233a, the pair of second drive wire receiving holes 233b, a pair of first fixing wire receiving holes (not illustrated), a pair of second fixing wire receiving holes (not illustrated), a central groove 242, a wire gripping portion 24, and an internal passage 231.

The pair of first drive wire receiving holes 233a may be a pair of holes into which the first drive wire 261 passing through the plurality of joint portions 22 is inserted along the longitudinal axis.

The pair of second drive wire receiving holes 233b may be a pair of holes into which the second drive wire 262 passing through the plurality of joint portions 22 is inserted along the longitudinal axis.

For example, when viewed from the longitudinal axis, the pair of first drive wire receiving holes 233a and the pair of second drive wire receiving holes 233b may be respectively formed at positions that overlap the pair of first drive wire passages 222a and the pair of second drive wire passages 222b formed in the plurality of joint portions 22.

The pair of first fixing wire receiving holes (not illustrated) may be formed in a portion spaced apart side by side from the center along the first virtual line perpendicular to the central axis.

The pair of second fixing wire receiving holes (not illustrated) may be formed in a portion spaced side by side from the center along the second virtual line perpendicular to the central axis.

For example, the pair of first fixing wire receiving holes (not illustrated) and the pair of second fixing wire receiving holes (not illustrated) may respectively have the same angle as those of the pair of first fixing wire passages 223a and the pair of second fixing wire passages 223b of the plurality of joint portions 22, and may form a passage having a convergent shape.

The wire gripping portion 24 may grip the first fixing wire 271 and the second fixing wire 272 that are inserted into the central groove 242 to be inserted into the distal portion 23.

For example, the wire gripping portion 24 may be formed of a material that is relatively more flexible than that of the distal portion 23. For example, the wire gripping portion 24 may include a conical shape with a cross-sectional width decreasing toward the longitudinal axis.

For example, the wire gripping portion 24 may include a first fixing passage 241a through which the first fixing wire 271 passes, and a second fixing passage 241b through which the second fixing wire 272 passes.

The first fixing passages 241a may be a pair of passages formed on a point spaced apart side by side from the center along the first virtual line perpendicular to the central axis.

The second fixing passages 241b may be a pair of passages formed on a point spaced apart side by side from the center along the second virtual line perpendicular to the central axis.

The first fixing passage 241a and the second fixing passage 241b may respectively have the same angle as those of the pair of first fixing wire passages 223a and the pair of second fixing wire passages 223b of the plurality of joint portions 22, and may form a passage having a convergent shape.

Therefore, the first fixing wire 271 passing through the pair of first fixing passages 241a along the longitudinal axis may perpendicularly cross the second fixing wire 272 passing through the pair of second fixing passages 241b.

One end of the first drive wire 261 may be connected to the first drive actuator 281, and the other end of the first drive wire 261 may be fixed to the distal portion 23 after sequentially passing through the proximal portion 21 and the plurality of joint portions 22. For example, the first drive wire 261 may be formed as a pair of wires spaced apart side by side and extending along the first virtual line.

One end of the second drive wire 262 may be connected to the second drive actuator 282, and the other end of the second drive wire 262 may be fixed to the distal portion 23 after sequentially passing through the proximal portion 21 and the plurality of joint portions 22. For example, the second drive wire 262 may be formed as a pair of wires spaced apart side by side and extending along the second virtual line.

According to the above-structure, the first drive wire 261 and the second drive wire 262 may pass on four points spaced apart at equal intervals radially along the edge periphery of the plurality of joint portions 22 in a state of being parallel with each other After passing through the first fixing wire passages 223a formed on one side with respect to the first virtual line among the pair of first fixing wire passages 223a, the first fixing wire 271 may pass through the first fixing wire passages 223a on the other side which are not passed through by changing a direction while passing through the first fixing passage 241a of the wire gripping portion 24, and as a result, may have a structure in which both ends protrude in a proximal direction to be connected to a first fixing actuator 291.

After passing through the second fixing wire passages 223b formed on one side with respect to the second virtual line among the pair of second fixing wire passages 223b, the second fixing wire 272 may pass through the second fixing wire passages 223b on the other side which are not passed through by changing a direction while passing through the second fixing passage 241b of the wire gripping portion 24, and as a result, may have a structure in which both ends protrude in a proximal direction to be connected to a second fixing actuator 292.

According to the above-structure, on the basis of a neutral state in which the flexible drive manipulator 2 is not driven as illustrated in FIG. 9, two strands of the first fixing wire 271 and the second fixing wire 272 each having both ends respectively connected to the first fixing actuator 291 and the second fixing actuator 292 may have a structure of converging symmetrically so as to have an oblique angle toward each other while passing through the plurality of joint portions 22.

The drive operator 28 may include a first drive actuator 281 configured to apply a tensile force to the first drive wire 261, and a second drive actuator 282 configured to apply a tensile force to the second drive wire 262.

The fixing operator 29 may include a first fixing actuator 291 configured to apply a tensile force to the first fixing wire 271, and a second fixing actuator 292 configured to apply a tensile force to the second fixing wire 272.

The controller 25 may drive the plurality of joint portions 22 along the first rotational direction by adjusting the tensile force applied to the first drive wire 261 through the first drive actuator 281. The controller 25 may drive the plurality of joint portions 22 along the second rotational direction by adjusting the tensile force applied to the second drive wire 262 through the second drive actuator 282.

The controller 25 may adjust supporting rigidity according to the first rotational direction of the plurality of joint portions 22 by adjusting the tensile force applied to the first fixing wire 271 through the first fixing actuator 291. The controller 25 may adjust supporting rigidity according to the second rotational direction of the plurality of joint portions 22 by adjusting the tensile force applied to the second fixing wire 272 through the second fixing actuator 292.

According to the flexible drive manipulator 2 according to an example embodiment, it is possible to drive the plurality of joint portions 22 with two degrees of freedom in the first rotational direction and the second rotation direction, and at the same time, it is possible to add rigidity so as to maintain a driving configuration in the first rotational direction and the second rotational direction.

According to the flexible drive manipulator 2 according to an example embodiment, it is possible to individually adjust driving and rigidity through two types of wire configurations of a drive wire and a fixing wire, and thus there is an advantage of being simple in terms of a structure and maintaining miniaturization.

According to the flexible drive manipulators 1 and 2 according to an example embodiment, it is possible to adjust a tensile force applied to a fixing wire, thereby implementing variable rigidity.

According to the flexible drive manipulators 1 and 2 according to an example embodiment, it is possible to stably support an operation of an end effector by increasing rigidity of a continuum manipulator. In addition, it may be possible to predict positions of distal ends of the flexible drive manipulators 1 and 2 only with a tensile model of a drive wire.

When the flexible drive manipulators 1 and 2 according to an example embodiment are applied to a surgical endoscope, it is possible to secure a channel through which a surgical instrument can pass through an internal passage of each of a plurality of joint portions even though the endoscope is bent in various configurations, and the endoscope may not sag easily even though a load and moment are applied to the endoscope.

Figure 13:
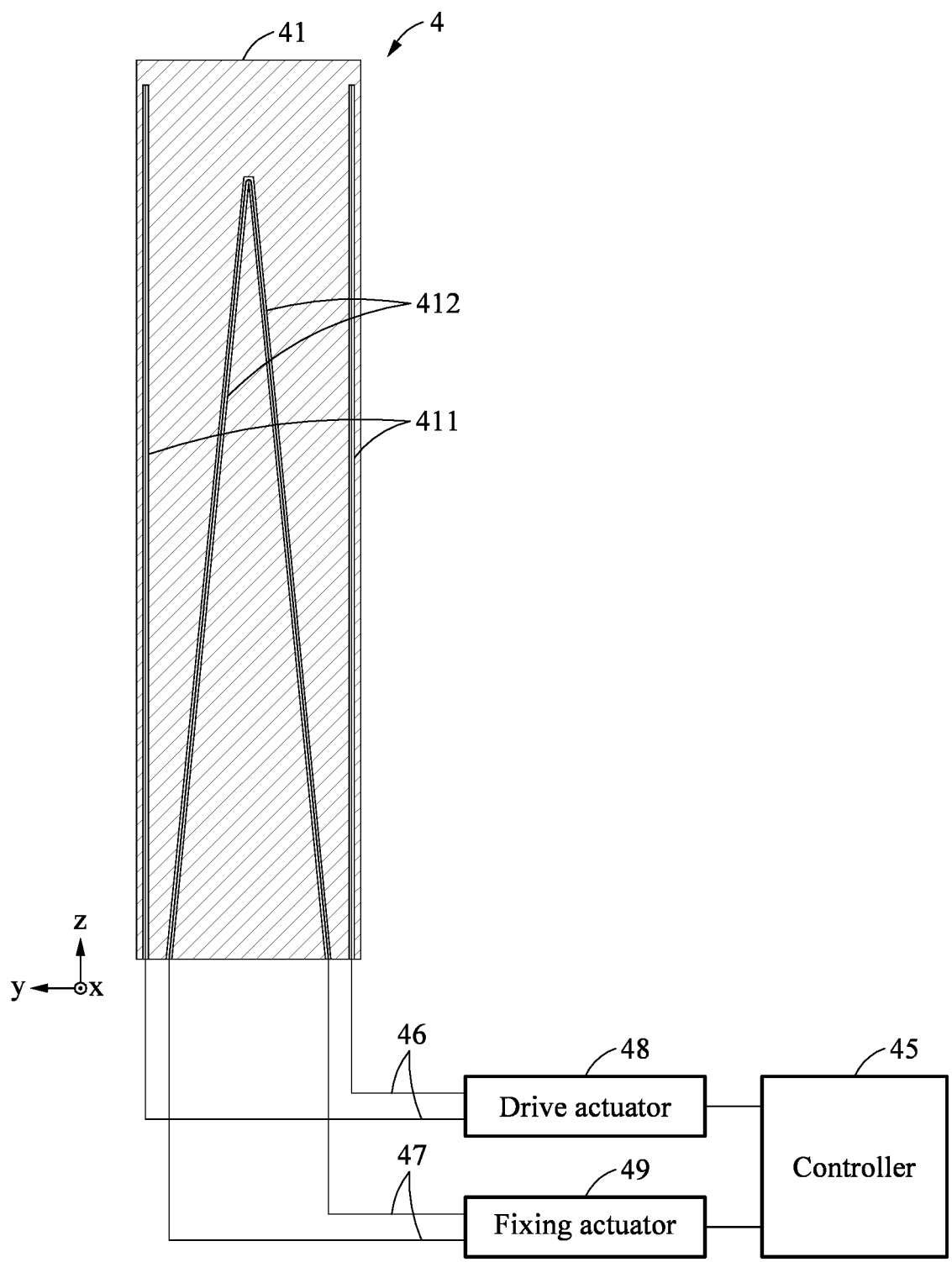
FIG. 13 is a cross-sectional view of a flexible drive manipulator according to an example embodiment.

FIG. 13 is a cross-sectional view of a flexible drive manipulator according to an example embodiment.

Referring to FIG. 13, unlike the flexible drive manipulators 1, 1', and 2 having a plurality of joint portions illustrated in FIGS. 1 to 12, a configuration of a flexible drive manipulator 4 having one deformable body can be confirmed.

The flexible drive manipulator 4 according to an example embodiment may include a flexible body 41 extending along a longitudinal axis (z-axis direction in FIG. 13) and having flexibility, a pair of drive wires 46 passing through an edge portion of the flexible body 41 in parallel along the longitudinal axis to drive the flexible body 41 in a rotational direction of rotation with respect to an axis perpendicular to the longitudinal axis, a fixing wire 47 passing through the flexible body 41 in a convergent shape along the longitudinal axis to adjust rigidity of the flexible body 41, a drive actuator 48 connected to the drive wire 46 to adjust a tensile force of the drive wire 46, a fixing actuator 49 connected to the fixing wire 47 to adjust a tensile force of the fixing wire 47, a controller 45 configured to control the drive actuator 48 and the fixing actuator 49.

The flexible body 41 may extend along the longitudinal axis to be flexibly curved.

For example, the flexible body 41 may include a pair of drive wire passages 411 in which both edge portions spaced apart along an axis perpendicular to a central axis are formed to be recessed along the longitudinal axis, and a fixing wire passage 412 formed as a pair of passages passing through points spaced apart from each other along the axis perpendicular to the central axis, and having an interval therebetween decreasing toward the longitudinal axis, the fixing wire passage 412 through which the fixing wire 47 passes.

The pair of drive wire passages 411 may be formed to be recessed on both edge portions of the flexible body 41 and both are in equilibrium with each other based on a state in which the flexible drive manipulator 4 stands upright along the longitudinal axis as illustrated in FIG. 13.

The fixing wire passage 412 may be formed to be recessed along the longitudinal axis at two points spaced apart inwardly from each of the pair of drive wire passages 411 along the axis perpendicular to the central axis as illustrated in FIG. 13, and may have a shape of converging to be obliquely inclined toward each other.

The pair of drive wires 46 may bend or extend the flexible body 41 in the rotational direction according to driving of the drive actuator 48.

The fixing wire 47 may adjust the rigidity of the flexible body 41 by driving of the fixing actuator 49.

According to the flexible drive manipulators 1, 2, and 4 according to an example embodiment, when the flexible drive manipulators 1, 2, and 4 need to move inside a narrow and curved tube, it is possible to allow the flexible drive manipulators 1, 2, and 4 to be in a state of low rigidity so that the flexible drive manipulators 1, 2, and 4 adapt to a shape of the tube and move, and then when the end effector reaches a driving position, it is possible to allow the flexible drive manipulators 1, 2, and 4 to be in a state of high rigidity so as to stably support driving of the end effector.

According to the flexible drive manipulators 1, 2, and 4 according to an example embodiment, it is possible to prevent a flexion phenomenon that occurs due to redundant degrees of freedom when only a conventional flat wire is used.

Figure 14:
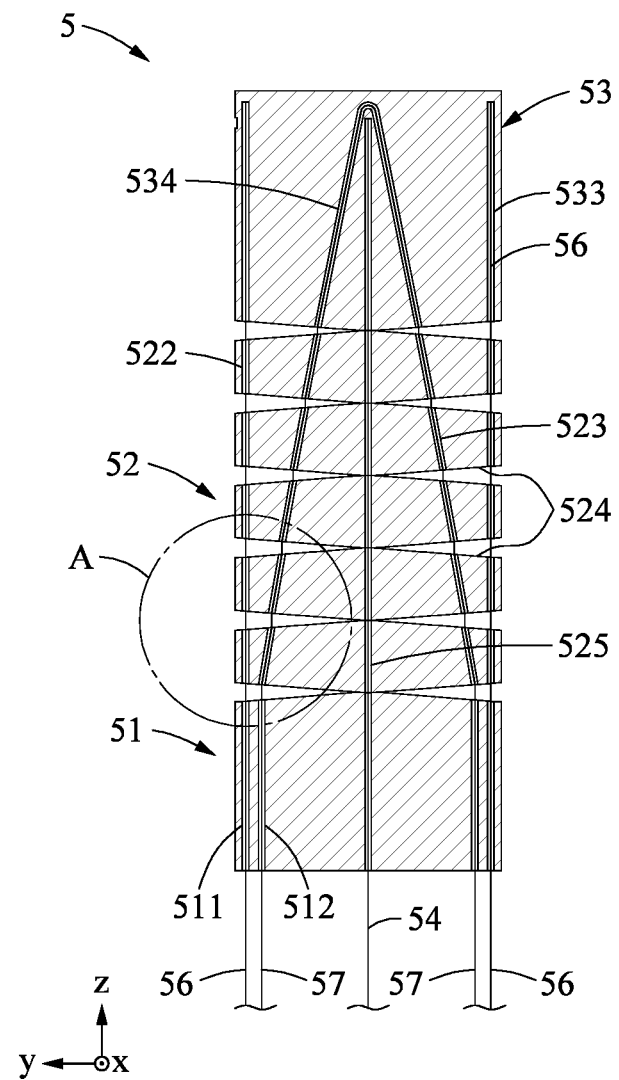
FIG. 14 is a cross-sectional view of a flexible drive manipulator according to an example embodiment.
Figure 15:
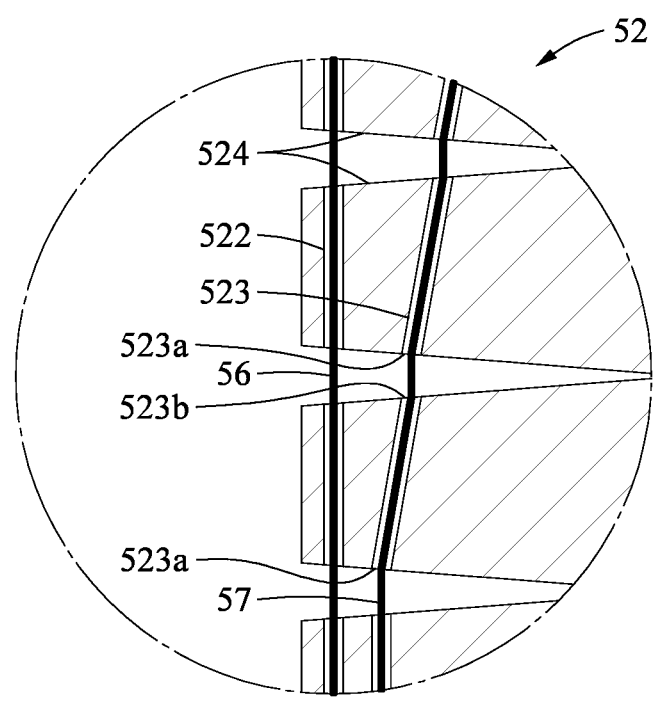
FIG. 15 is an enlarged cross-sectional view of a region A of FIG. 14.

FIG. 14 is a cross-sectional view of a flexible drive manipulator according to an example embodiment, and FIG. 15 is an enlarged cross-sectional view of a region A of FIG. 14.

Referring to FIGS. 14 and 15, a configuration of a flexible drive manipulator 5 having a configuration different from those of the flexible drive manipulators 1, 1', 2, and 4 of the example embodiments illustrated in FIGS. 1 to 13 can be confirmed.

The flexible drive manipulator 5 according to an example embodiment may include a proximal portion 51 serving as a reference for driving, a plurality of joint portions 52 drivably connected from an end of the proximal portion 51 with respect to a longitudinal axis, a distal portion 53 connected to an end of the plurality of joint portions 52, a drive wire 56 passing through the plurality of joint portions 52 in parallel along the longitudinal axis to drive the plurality of joint portions 12 in a rotational direction with respect to an axis (x-axis in FIG. 14) perpendicular to the longitudinal axis, a fixing wire 57 passing through the plurality of joint portions 52 in a shape of converging along the longitudinal axis to adjust rigidity of the plurality of joint portions 12, and a central wire 54 passing through centers of the plurality of joint portions 52 along the longitudinal axis to be fixed to the distal portion 53.

A portion of the drive wire 56 passing between the plurality of joint portions 52 may be parallel with the longitudinal axis (z-axis in FIGS. 14 and 15).

For example, the plurality of joint portions 52 may include a pair of contact portions 524 in which both edge portions are formed to be recessed along the longitudinal axis along a transverse direction perpendicular to a central axis of the joint portion 52 parallel with the longitudinal axis, a pair of drive wire passages 522 through which the drive wire 56 passes in parallel with the central axis of the joint portion 52, a pair of fixing wire passages 523 having an inclination of converging with respect to the central axis of each joint portion 52 as a distance to the distal portion 53 decreases, and a central wire passage 525 through which the central wire 54 passes along the central axis.

For example, the pair of fixing wire passages 523 may be inclined with respect to the central axis of the joint portion 52 and at the same time, may be formed symmetrically to each other with respect to the central axis.

As another example, it should be noted that the pair of contact portions 524 may be formed only on any one surface, unlike being formed on both sides of the joint portion 52 as illustrated in FIGS. 14 and 15.

The pair of drive wire passages 522, the pair of fixing wire passages 523, and the central wire passage 525 formed in the joint portion 52 may be positioned on the same line along the central axis (z-axis in the drawing) of the joint portion 52.

As a joint portion 52 among the plurality of joint portions 52 is connected adjacent to the distal portion 53, an interval between the pair of fixing wire passages 523 of each of the joint portions 52 may sequentially decrease.

For example, the fixing wire passage 523 may include a front opening 523b exposed toward the distal portion 53, and a rear opening 523a exposed toward the proximal portion 51.

Since the pair of fixing wire passages 523 have a structure having an inclination of converging with each other toward the distal portion 53, a position of the front opening 523b of the joint portion 52 may be formed closer to the center than a position of the rear opening 523a of the joint portion 52. That is, the front opening 523b may be formed at a position closer to the central axis of the corresponding joint portion 52 than that of the rear opening 523a.

Among the pair of joint portions 52 connected adjacent to each other, the rear opening 523a of a joint portion 52 relatively adjacent to the proximal portion 51 and the front opening 523b of a joint portion 52 relatively adjacent to the distal portion 53 may be positioned on the same line parallel with the longitudinal axis.

In other words, in a neutral state in which the plurality of joint portions 52 are not bent as illustrated in FIG. 15, among the pair of joint portions 52 connected adjacent to each other along the longitudinal axis, the front opening 523b and the rear opening 523a of each of the pair of joint portions 52 facing each other may accurately overlap along a direction parallel with the longitudinal axis.

As illustrated in FIG. 15, a virtual straight line connecting between openings of the fixing wire passages 523 of each of the two joint portions 52 connected adjacent to each other may be parallel with the longitudinal axis or the central axis of the joint portion 52.

Therefore, whereas the fixing wires 17, 271, and 272 of the flexible drive manipulators 1, 1', and 2 illustrated in FIGS. 5, 8, and 10 form a path having a shape of decreasing symmetrically and linearly as a distance to proximal decreases along the longitudinal axis, a pass-through path of the fixing wire 57 of the flexible drive manipulator 5 according to an example embodiment may form an inclination of converging to the central axis of the joint portion 52 only in a section passing through the fixing wire passage 523, and may be parallel with the central axis of the joint portion 52 that has been previously passed through in a section connected between the plurality of joint portions 52.

According to the above-structure, when the flexible drive manipulator 5 is bent along one direction through a tensile force applied to the pair of drive wires 56, the contact portion 524 of each of the joint portions 52 adjacent to each other may rotate so as to be in close contact with the oppositely connected joint portion 52, and accordingly shapes of the openings 523a and 523b of the fixing wire passages 523 on both joint portions 52 may be engaged with each other to be in close contact.

As a result, in a process of the plurality of joint portions 52 being bent, the front opening 523b and the rear opening 523a of each of the two contacting portions 524 facing each other may be engaged at an accurate position, thereby preventing a problem in which the fixing wire 57 exposed between the both openings 523a and 523b is caught between the both contact portions 524.

In addition, in a process in which the joint portions 52 adjacent to each other are in rolling contact, an angle formed by the fixing wire 57 connected between the respective fixing wire passages 523 of the both joint portions 52 may be maintained to have a value between angles formed by respective central axes of the both joint portions 52, thereby preventing a magnitude and a direction of a tensile force formed for each section of the fixing wire 57 from being dispersed.

In addition, the fixing wire 57 may maintain an area projected on each of the opposite two contact portions 524 at a minimum level, thereby effectively reducing a tendency of the fixing wire 57 to be interfered between the contact portions 524.

Although the example embodiments have been described with reference to the limited drawings as described above, various modifications and changes may be made from the foregoing descriptions by those skilled in the art. For example, suitable results can be achieved even if the described techniques are performed in a different order, and/or even if components of the described structure, device, and the like are coupled or combined in a different manner, or are replaced or substituted by other components or their equivalents.

The invention claimed is:

1. A flexible drive manipulator comprising:
a proximal portion;
a plurality of joint portions drivably connected from an end of the proximal portion with respect to a longitudinal axis;
a distal portion connected to an end of the plurality of joint portions;
a pair of drive wires passing through the plurality of joint portions in parallel along the longitudinal axis, the pair of drive wires configured to drive the plurality of joint portions in a rotational direction of rotation with respect to a transverse axis perpendicular to the longitudinal axis; and
a fixing wire passing through the plurality of joint portions in a shape of converging along the longitudinal axis, the fixing wire configured to adjust a rigidity of the plurality of joint portions.

2. The flexible drive manipulator of claim 1, wherein the joint portions comprise:
a pair of contact portions in which both edge portions spaced along a transverse axis perpendicular to a central axis of the joint portion parallel with the longitudinal axis are formed to be recessed along the longitudinal axis; and
a pair of fixing wire passages through one of which the fixing wire passes, the pair of fixing wire passages having an inclined shape so as to converge symmetrically to each other with respect to the longitudinal axis,
axis an interval between the fixing wire passages sequentially decrease among the plurality of joint portions along a direction toward the distal portion.

3. The flexible drive manipulator of claim 2, wherein the fixing wire passages comprise:
a front opening exposed toward the proximal portion; and
a rear opening exposed toward the distal portion, and
among a pair of joint portions connected adjacent to each other, the rear opening of a joint portion that faces towards the proximal portion and the front opening of a joint portion that faces towards the distal portion are positioned on the same line parallel with the longitudinal axis.

4. The flexible drive manipulator of claim 3, wherein
a contact portion of each of a plurality of joint portions rotates so as to be in close contact with an oppositely connected joint portion by a tensile force applied to the pair of drive wires, and
among a pair of joint portions contacting adjacent to each other, the rear opening of a joint portion that faces towards the proximal portion and the front opening of a joint portion that faces towards the distal portion are in close contact with each other so that shapes of respective openings are engaged with each other.

5. The flexible drive manipulator of claim 3, wherein
a portion of the fixing wire passing through respective fixing wire passages of the plurality of joint portions has an inclination of converging toward a central axis of each of the plurality of joint portions, and a portion of the fixing wire passing between the plurality of joint portions is parallel with a central axis of a joint portion that has been previously passed through.

6. The flexible drive manipulator of claim 2, further comprising:
a central wire passing through central axes of the plurality of joint portions, the central wire fixed to the distal portion,
wherein the joint portions further comprise:
a pair of drive wire passages formed to be spaced apart along the transverse axis with respect to the central axis, the pair of drive wire passages through which the pair of drive wires pass; and
a central wire passage through which the central wire passes along the central axis.

7. The flexible drive manipulator of claim 6, wherein the pair of drive wire passages, the pair of fixing wire passages, and the central wire passage of the joint portion are positioned on the same line along a traverse axis perpendicular to the central axis of the joint portion.

* * * * *